United States Patent [19]

Hassler

[11] 4,235,111
[45] Nov. 25, 1980

[54] APPARATUS FOR ULTRASONIC SCANNING

[75] Inventor: Dieter Hassler, Erlangen, Fed. Rep. of Germany

[73] Assignee: Siemens Aktiengesellschaft, Berlin & Munich, Fed. Rep. of Germany

[21] Appl. No.: 830,173

[22] Filed: Aug. 31, 1977

[30] Foreign Application Priority Data

Sep. 29, 1976 [DE] Fed. Rep. of Germany ....... 2643918

[51] Int. Cl.³ .............................................. G01N 29/00
[52] U.S. Cl. ............................ 73/626; 128/2.052;2 V
[58] Field of Search ................ 73/625, 626, 628, 610, 73/611, 612; 340/5 R, 5 MP, 9; 367/7, 105, 103

[56] References Cited

U.S. PATENT DOCUMENTS

| 3,881,466 | 5/1975 | Wilcox | 73/626 |
|---|---|---|---|
| 3,895,525 | 7/1975 | Eichelberger et al. | 73/626 |
| 3,911,730 | 10/1975 | Niklas | 73/626 |
| 3,919,683 | 11/1975 | Itamura et al. | 73/626 |
| 3,936,791 | 2/1976 | Kossoff | 73/626 |
| 4,161,121 | 7/1979 | Zitelli et al. | 73/626 |

FOREIGN PATENT DOCUMENTS 941573 11/1963 United Kingdom ...................... 73/626

Primary Examiner—Stephen A. Kreitman
Attorney, Agent, or Firm—Hill, Van Santen, Steadman, Chiara & Simpson

[57] ABSTRACT

In an illustrated embodiment an array of ultrasonic transducer elements is combined into a first transmitting surface to emit a first transmit signal, and then in alternation with blanking intervals is combined into receiving surfaces of progressively increased size for the reception of echo signals and for constructing a first image line of a first partial image. A second transmitting surface of lesser size then emits a transmit signal and further combinations of transducer elements are activated during time intervals thereafter which correspond to the blanking intervals of the first image line. Such sequential lines may form a composite line on a visual display. A planar array of transducer elements may have its successive receiving surfaces of varying size electronically focused either in the scan direction or in the layer thickness direction, or the array can have mechanical curvature to provide a desired focus in the layer direction. A circuit arrangement is preferred which simplifies the control of switching and minimizes the number of electronic focusing channels while still achieving a relatively high image frequency.

20 Claims, 6 Drawing Figures

78 Control Logic

APPARATUS FOR ULTRASONIC SCANNING

BACKGROUND OF THE INVENTION

The invention relates to an apparatus for the purpose of ultrasonic scanning comprising an ultrasonic applicator including a plurality of ultrasonic transducers spatially adjacently arranged in a plane surface and a control device which effects an equiphase-connection of a number of ultrasonic transducers-corresponding to the desired focus distance-to a signal transmitter, or a signal receiver, respectively.

Known apparatus of this type make possible linear scanning with a shifting adaptation of the focus without an excessively great technical outlay merely by a multiple exposure of one and the same line to ultrasonic waves including a transmitting surface which changes gradually (or in step-by-step-fashion). However, this results in an unnecessary increase in the time consumed for the image construction.

SUMMARY OF THE INVENTION

It is the object of the present invention to construct an apparatus for ultrasonic scanning of the type initially cited which avoids this disadvantage of the known apparatus without resulting in an increase in the technical outlay and possessing the desired optimum image frequency and image quality.

The object is achieved in accordance with the invention by virtue of the fact that the control device for the transducer elements is so constructed that, given a predetermined transmitting surface of the transducer elements, said control device changes the receiving surface in the receiving mode after emission of a transmitting signal such as to effect a change in the receiving surface size from a low value to a maximum value.

The invention makes possible an adaptation of the focus, pursuant to a single emission of a transmitting pulse per line, in different receiving surfaces while the construction of the image line is still in progress. A scanning apparatus is thus produced which, operating according to the principle of the concomitant natural focus, renders possible an optimum image definition in the desired depth range with a substantially increased image frequency and simultaneously requiring the least amount of technical outlay. An advantageous embodiment of the invention specifies that the control device is to select each of the receiving surfaces to be successively adjusted to be of such a size that the resulting depth positions of the natural focus correspond to those depths from which echos emanating from body structures are expected. For this purpose, a change in the receiving surface should also take place through a change in the surface width as well as through a change in the surface height. This results in a depth-dependent adaptation of the transmitting/receiving surface both in the transverse direction and in the direction of the layer thickness of the ultrasonic scanning beam. Thus, with a markedly improved transverse resolution, the layer thickness contrast is also simultaneously improved. Thus also in the case of a relatively great layer thickness, even those contrast lines which are not positioned vertically to the scanning plane are sharply reproduced. However, the layer density should be in a suitable ratio relative to the transverse dimension. Expediently, in the case of natural focusing, this layer thickness should not be exceeded by the associated transverse dimension of the sonic beam by more than a factor of two. In a further development of the invention, this can be realized in a simply manner by virtue of the fact that, for each of the receiving surfaces to be successively adjusted, the surface width determining the transverse dimensions of the sonic beam is maximally selected to be approximately greater by the factor of two than the area height which determines the layer thickness detected by the sonic beam. In a further advantageous embodiment of the invention, an additional improvement in the transverse resolution can be achieved by allocating to the control device additional means for an electronic simulation of a one dimensional curved entire surface of all the transducer elements. In contrast with mechanically focused ultrasonic transducer arrays, the ultrasonic waves emanating from the focal point reach the plane; i.e., the mechanically planar transducer surface in the different transducer columns at different times; due to the different phasepositions, an addition of all component waves can lead to mutual extinction. However, if separate receiving channels are formed and if those particular delay times are electrically connected to the electric receiving signal of the individual transducer elements of each column of the transducer element array, which delay times the acoustic signals have been subjected to while passing through the path from the planar transducer element array to the curved surface, and if the electric signals are then added, an electronic focusing is achieved. The apparent curvature, produced in this manner, of the transducer element array which is planar per se, can be changed by the selection of delay times, whereby, for example, according to the mechanically prefocused transducer of the British Letters Pat. No. 941,573, the focal point is displaced, i.e., the focal distance of the transducer array is changed. However, in the apparatus according to the invention, natural and electronic focusing should expediently occur in successive circuit-stages.

Further advantageous embodiments of the invention are apparent from the detailed description and claims. In particular, reference may be made to circuit details for minimizing the time required for reconfiguration of transmit and receive surfaces and for reconfiguring the electronic focusing channels during successive transmit/receive cycles. The disclosed circuit concepts are technically extremely simple and thus also especially economical. The control members herein disclosed render possible a simple and rapid reprogramming or new-programming of the scan cycle. In addition, the scanning by means of partial images renders possible the insertion of so-called blanking intervals by means of which switching transients resulting from actuation of the control switches are suppressed.

Other important objects, features and advantages of the present invention will be apparent from the following detailed description of an illustrative embodiment, taken in connection with the accompanying sheets of drawings.

DETAILED DESCRIPTION

Figure 1:
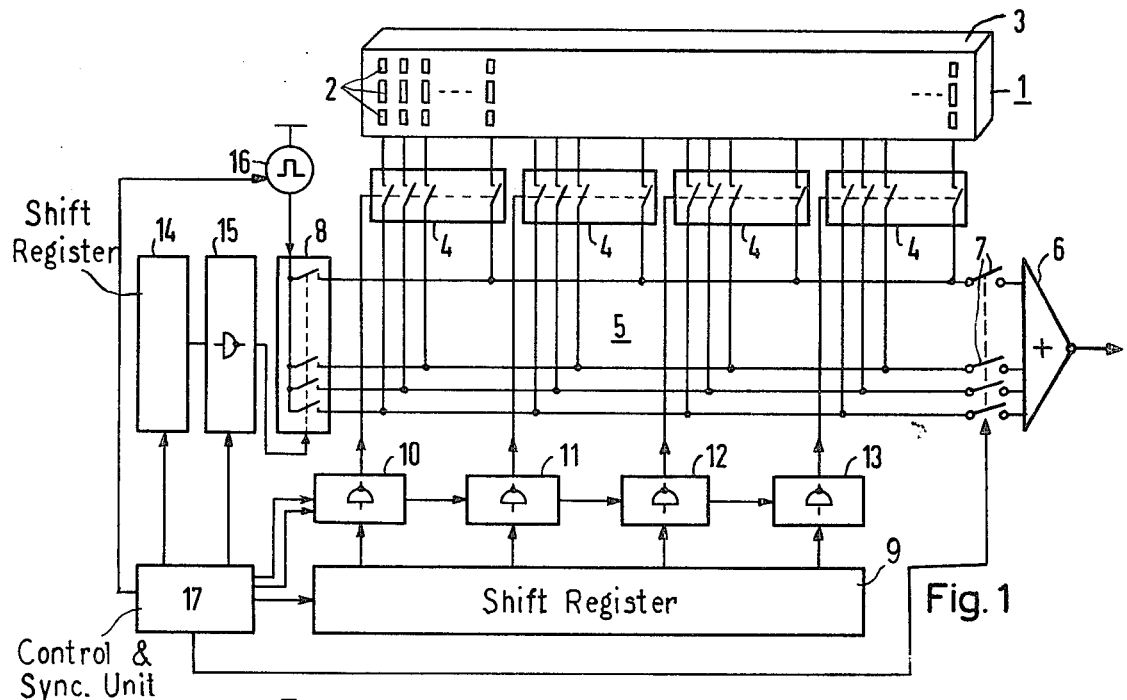
FIG. 1 illustrates in a basic circuit diagram a sample embodiment for the purpose of producing a concomitant natural focus in the case of planar ultrasonic transducer arrangements.
Figure 4:
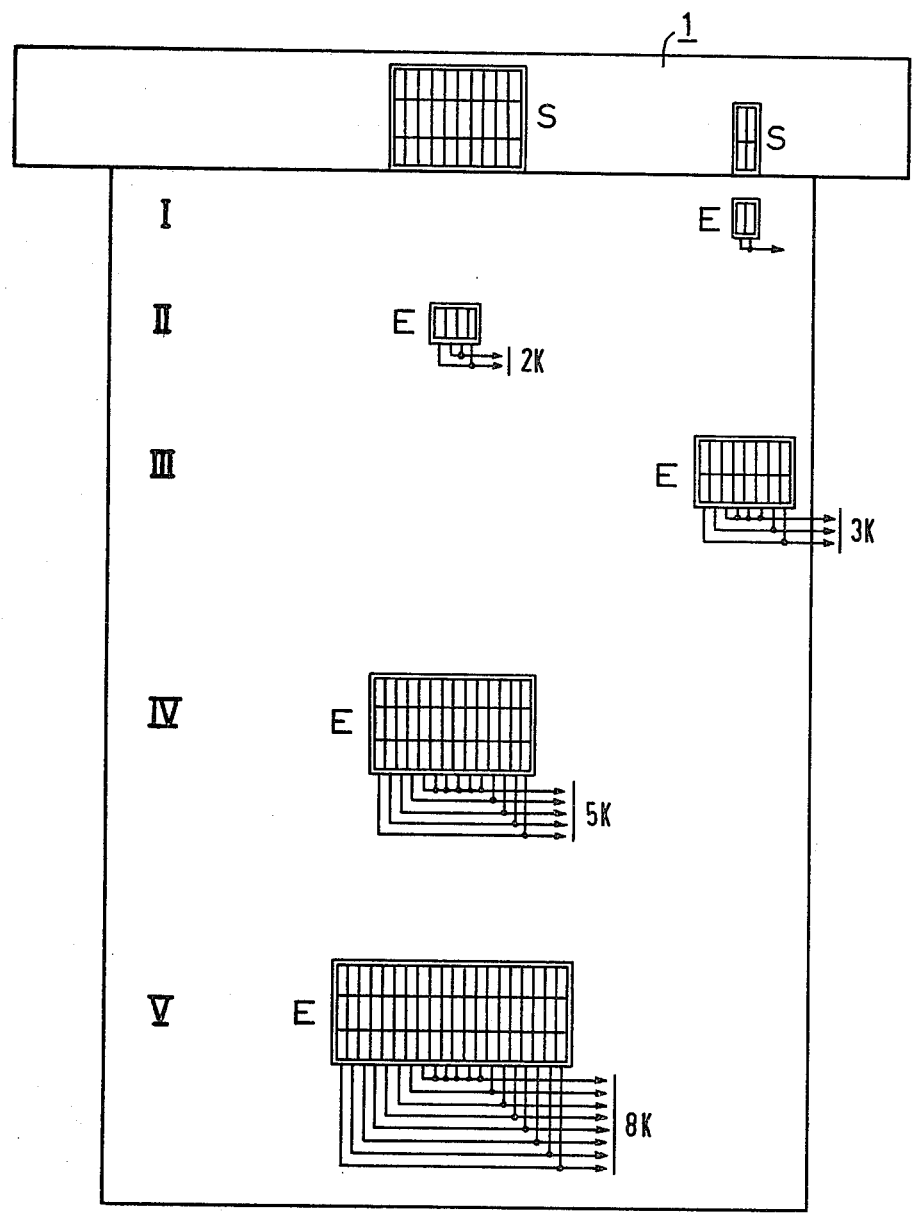
FIG. 4 illustrates the possible image construction by means of ultrasonic arrays according to FIGS. 1 through 3 with blanking intervals in the case of a concomitant natural focus and with an additional focusing.

In FIG. 1, an ultrasonic array is designated by reference numeral 1. It is composed of a plurality of ultrasonic transducer elements 2 which are arranged on the application surface of a carrier section 3 in several superimposed rows. In the present sample embodiment, the array comprises preferably eighty columns each having three superimposed transducer elements 2. The operating frequency preferably amounts to about two megahertz (2 MHz). Thus, with a column width of approximately two millimeters (transducer element width plus interstice), an ultrasonic image results which is constructed e.g. of about sixty lines and has a scanning width of approximately 12 cm and a scanning depth of approximately 18 cm. With the sample embodiment according to FIG. 1, a total of approximately five fixed depths of receiver focus are to be automatically switched into effect during a scanning sequence. The receiving surface thus as indicated in FIG. 4 automatically varies between a minimum of two adjacent plates of the central transducer element row on the array (mode I in FIG. 4) and a maximum of twenty columns (in the case of additional electronic focusing) consisting of all three transducer element rows (mode V in FIG. 4). When there is additional focusing, at the most eight channels for different delay times are required. The number of channels (K) used for each mode in FIG. 4 are indicated by the numeral preceding the letter K. The aforementioned data has been selected (in using approximate formulas) such that, in the case of an electronic concomitant focus, the six decibel values (6 dBvalues) of the effective sonic beam width remain constantly at approximately four millimeters (4 mm) over the entire image depth. Thus, the class of image quality of conventional mechanically-moved ultrasonic scanning systems with a high image frequency is achieved. The layer thickness of the scanning fluctuates between three and eight millimeters (3 and 8 mm). However, other values correspondingly result for other operating frequencies which also comprise differently dimensioned arrays with e.g. a greater number of columns and an accordingly greater number of lines. The image dimensions fluctuate correspondingly and, accordingly, variant fixed depths of the receiving focus with correspondingly varying transmitting/receiving surfaces result.

Figure 2:
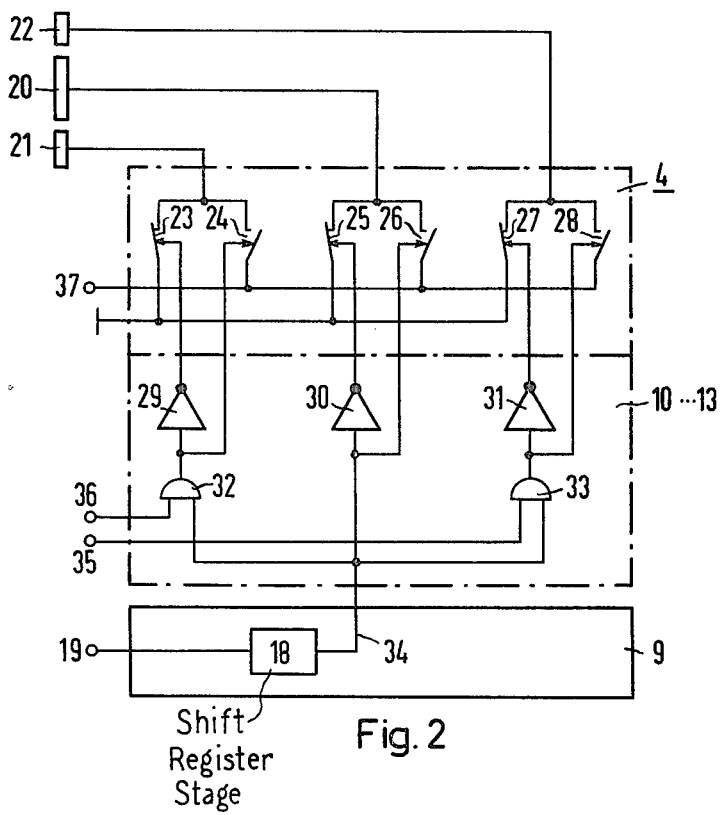
FIG. 2 illustrates a possible embodiment of a surface pattern circuit with a logic unit and a shift register stage for actuating a column of three superimposed transducer elements of an ultrasonic array such as shown in FIG. 1.
Figure 3:
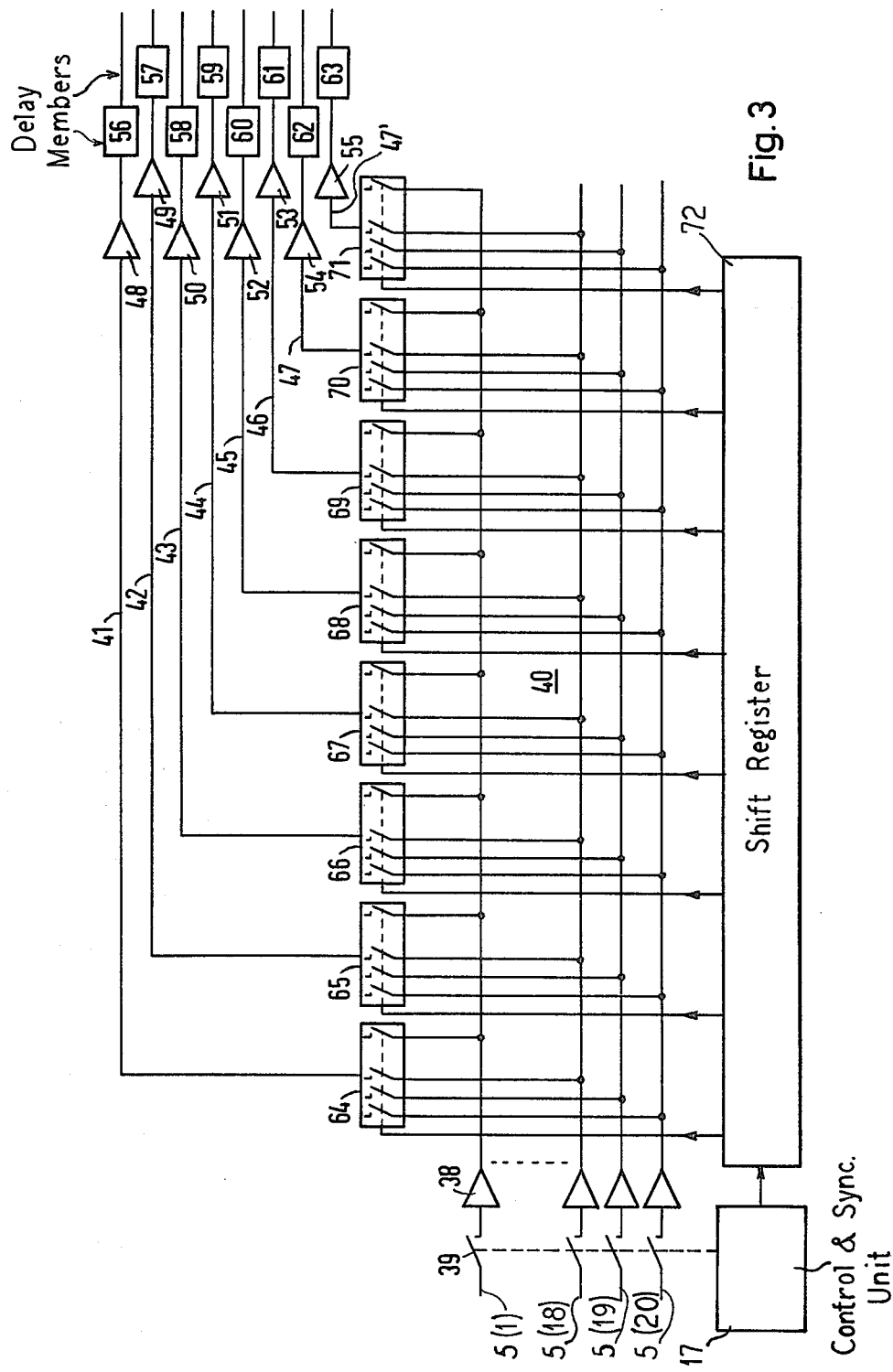
FIG. 3 illustrates a basic circuit diagram for the realization of an additional electronic focusing.

In the present applied instance, the object of the signal processing consists in reducing the data available from a total of $3 \times 80$ transducer element plates 2 (acting as signal sources) to a single signal in the case of purely natural focusing (e.g. as in FIG. 1 alone); or, in the case of additional electronic focusing (e.g. as shown in FIG. 3), to first reduce said data to eight signals and then, after a delay, to also reduce it to one signal. Essentially, there are four functions which must be satisfied here. On the one hand, the position of the effective radiator or of the ultrasonic line to be constructed in the ultrasonic image must be defined. On the other hand, the transmitting/receiving surface-width of the effective radiator as well as its transmitting/receiving surface-height must be determined. Finally, a chronologically correct switching over between transmission and reception must be guaranteed. Theoretically, it is possible to carry out a circuit reduction to one channel with a series switch per ultrasonic vibrating plate. For a direct reduction to a total of eight channels (without an intermediate stage), eight series switches for each plate 2 would be necessary; i.e., thus, $8 \times 240 = 1920$ individual switches. Regarding the latter instance, however, a less costly solution results if redundancies are avoided and at least one intermediate stage of reduction is formed. Therefore, in order to achieve a certain unit-by-unit expansibility, a total of two successive stages are selected for the signal processing, which stages can be used selectively in combination or also individually. The first expansion stage makes possible a scanning according to the principle of the concomitant natural focus (basic circuit diagram according to FIG. 1); in contrast thereto, the second expansion stage makes possible an additional electronic focusing (basic circuit diagram according to FIG. 3). Both stages have been judiciously selected such that a new programming or a reprogramming of switch positions can be carried out easily and rapidly while the construction of an image line is still in progress. By creating so-called blanking intervals, interferences caused by the influence of control signal on transmitting (or receiving) channels are eliminated to a great extent, as shall be further explained in the following. Regarding the sample embodiment according to FIG. 1, the circuit-reduction results in such a manner that the array consisting of $3 \times 80$ individual transducer elements 2 is interconnected in a matrix-fashion on an intermediate plane consisting of a total of twenty so-called bus bars or matrix conductors 5, said interconnection proceeding via a total of $3 \times 80$ switching members (FIG. 2) which comprise an implementation of blocks 4, and are referred to in the following as surface pattern switches. In the sample embodiment according to FIG. 1, the signals of all twenty bars 5, in the receiving instance, are returned to one signal in a summation amplifier 6 (buffer amplifier) via a series connected receiving switch 7. If, however, additional electronic focusing subsequently is selected—for example, in accordance with the basic circuit diagram of FIG. 3—all twenty bars 5 are connected separately, via one receiving switch (39, FIG. 3) and associated buffer amplifier (38, FIG. 3) each, to the following circuit. In the transmitting instance, transmit switches 8 assume the distribution of the transmit signal to the individual bars 5. In order to actuate the surface-pattern switches of blocks 4 there is a first shift register 9 with logic blocks 10 through 13. Actuation of the transmit switches 8, however, is controlled by means of a second shift register 14 with the actuating logic 15. Component 16 represents the transmitting oscillator for feeding transducer elements 2 which are to be activated in the case of transmission. Block 17 is a control-and synchronization-unit for shift registers 9 and 14, and logic blocks 10 through 13; and 15. The functions of the above type which are to be carried out require an additional break-down. For this purpose, array 1 comprising transducer elements 2 is divided for actuation into a total of four similar blocks each with twenty transducer columns. Altogether twenty columns define the entire area of the largest receiving surface (mode V, FIG. 4) to be adjusted in an applied instance (natural and electronic). Each transducer element column of such a block then again represents the previously above-described sub-unit consisting of three switches of one of the blocks of the surface pattern switches 4 which are to be actuated separately. The number three results from the maximum number of transducer element rows provided per array. In the sample embodiment according to FIG. 1, the 80-bit-shift register 9, in addition to defining the fixedly preselected maximum surface width of the largest receiving block (mode V, FIG. 4), also defines the position of the image line to be constructed. Thus, proceeding from left to right, twenty bits are recorded into shift register 9 in block formation, for example at the twenty left most register stages, and, for the purpose of stepping (or advancing) the image line, the twenty bit-block is advanced (to the right as viewed in FIG. 1) one bit each time in the clock pulse (or cadence) of the line. Logic blocks 10 through 13, which are connected to shift register 9, serve the purpose of determining the height of the transmit/receive surface. Depending upon the preselected program cycle, these logic blocks convey the position data supplied by shift register 9 either to all the rows of the transducer blocks or to only a fraction thereof. The twenty bit-shift register 14, in connection with transmit switches 8, serves the purpose of determining the respective surface width. Transmit switches 8, which are dependent upon the data of shift register 14, activate only as many bars 5 as correspond to the desired width of the transmit field. In the receiving mode, transmit switches 8 may be actuated to prevent transmission of echo signals from certain of the transducer element columns, even though such columns have been enabled by means of shift register 9 as shown in FIG. 2. Thus, referring, for example, to FIG. 2, if register stage 18 contains a "one" bit, switch 26 will be closed, and an echo signal received by transducer 20 will not be short circuited to ground via switch 25, but will be conducted via closed switch 26 to terminal 37 and then to the associated one of the matrix conductors 5. If, however, the particular switch 8 which is associated with such matrix conductor is actuated to provide ground potential thereto, then such echo signal will not reach amplifier 6, FIG. 1, even though switch 26 is closed. Of course, in this mode of operation, the individual matrix conductors must be isolated so that grounding of one matrix conductor will not prevent transmission of echo signals via other of the matrix conductors to the summing amplifier 6. The provision of such isolation in conjunction with a summing amplifier is well understood by those skilled in the art. In the transmitting mode, the matrix conductors 5 are again electrically isolated so that a transmit pulse applied to one matrix conductor is not coupled to matrix conductors having an associated open switch 8. At the instant of transmission, the buffer amplifier 6, FIG. 1, or amplifiers 38, FIG. 3, are temporarily cut off from the transmitting energy by the input switch 7, FIG. 1, or switches 39, FIG. 3.

The actuating scheme described renders possible a simple and rapid programming. The height and width of the transmit/receive surfaces which may be changed most frequently are controlled by means of a rapidly switchable logic 10 through 13, or merely by means of a short shift register 14, respectively. Logic 15 between the short shift register 14 and the transmit switches 8 thus permits a reprogramming or new-programming of the shift register 14 without interference problems which would be caused by the concurrent actuating of the transmit switches 8. The formation of an intermediate plane consisting of twenty connective bars or matrix conductors 5 has the additional advantage in that the problem of loading an individual channel with the unavoidable capacitance of connected switches in the opened state is diminished.

FIG. 2 illustrates in the manner of a circuit segment the fundamental circuit for controlling the transducer elements of a single transducer column. An individual illustration of a flip-flop-register location 18 of shift register 9 with the respective actuating line 19 is immediately apparent. The actuation of the three individual radiators 20 through 22, arranged in a column one above the other, and different in area (the center element 20 being constructed to be of greater area than the elements 22 and 21 arranged above and below) proceeds by switching stages each comprising two surface pattern switches 23, 24, or 25, 26, or 27, 28, respectively, which operate in a push-pull fashion in relation to one another. The switching logic for the surface pattern switches comprises three inversion members 29, 30, 31, as well as AND-members 32, 33, which are interconnected as well as being connected to the output control line 34 of the flip-flop register stage 18 of shift register 9, on the one hand, and to two external controls 35, or 36, respectively of the control and synchronization unit 17 (FIG. 1), on the other hand. If a "one" is present at the output of flip-flop register stage 18 of shift register 9, switch 26 is closed and transmitting energy is supplied to the center transducer element 20 via transmit input 37 with switch 25 opened. The actuation of the further transducer elements 21 or 22, respectively, proceeds via control lines, 35, 36. If a "zero" is connected to both control lines, both transducer elements 21 or 22 are switched off. An additional connection of one or both transducer elements 21, 22, along with the center transducer element 20 results, if a "one" is connected to one or both of the control lines 35 and 36.

If an additional concomitant electronic focusing is desired, the circuit diagram according to FIG. 1 must be expanded correspondingly by that of FIG. 3. The problem existing here consists in distributing the signals of now all twenty bars of the barmatrix 5 according to FIG. 1 over a total of eight channels with varying delay times. The total number of eight channels is the result of the requirement for as low as possible a self-(or inherent, or natural) directional effect on the part of the receiving columns with a given receiving surface width and a given focal distance. The division of the receiver width into a finite as opposed to an infinite number of columns or channels, respectively, of varying electronic delay times results in a quantization error which is not permitted to exceed a specific quantity. This quantity amounts of one-eighth of the ultrasonic wavelength, from which the minimal number of channels is also derived. In the case of preselection of only eight channels, the allocation of individual columns to the channels must be changed while the construction of an image line is still in progress. With a reduced circuit complexity, however, this necessitates a reprogramming during the line construction. However, if a total of ten channels is employed for the purpose of signal delay, the allocation of the columns to the channels can be kept constant with the program remaining the same;

however, the circuit complexity is correspondingly great. Accordingly, with an additional electronic focusing, there is provided the connection of the fundamental circuit diagram according to FIG. 3 with that of FIG. 1 via a total of twenty buffer amplifiers 38 with input channel switches 39. In the arrangement illustrated in FIG. 3, each of the matrix conductors 5 of FIG. 1 is entirely electrically isolated from the other matrix conductors, and such entirely separate matrix conductors have been designated 5 (1) through 5 (20) at the left in FIG. 3. Thus, in FIG. 3, the matrix conductor 5 (1) is only connected with the twentieth switch position of each of the blocks 4 in FIG. 1 and is not connected with any of the other matrix conductors such as 5 (18), 5 (19) and 5 (20) which are actually shown at the left in FIG. 3.

Disposed at the outputs of the twenty buffer amplifiers 38, FIG. 3, there are the twenty further bus bars of a matrix 40. Each of these bars is now capable of being interconnected into a total of eight individual channels 41 through 47, 47' having a total of eight channel amplifiers 48 through 55 with outlet-connected delay members 56 through 63 providing respective different delay times. Analog switches integrated into packets 64 through 71 serve the purpose of selective connection. The position of all 20×8=160 individual switches is difined by a 160 bit-shift register 72. With the basic circuit diagram according to FIG. 3, the electronic focusing is to be laid out such that the focus lies on the axis of symmetry in front of the respective receiving surface. Accordingly, columns disposed symmetrically to this axis can be associated with the same delay channels. This symmetry requirement makes possible an additional economizing of individual channels. A control program for shift register 72, which makes possible a symmetrization of this type (in utilizing the minimum number of eight channels), shall be explained in greater detail in the following within the framework of the image construction-functional description of the basic circuit diagrams according to FIGS. 1 and 3.

In accordance with the invention, the surface patterns for transmission and reception in the case of a concomitant actual and/or electronic focusing must be connected at the amplifier input during the construction of an image line. If switching is effected in a relatively large time interval after the transmit pulse; i.e., at times which correspond to a great image depth, the transit-time-dependent amplification of the amplication depth compensation has reached high values. In such instances, a switchover which is particularly free of interference voltage is necessary. The most aggravating interferences are cross-talk pulses arriving from the control line of the respective control switches to the receiving line. These cross-talk pulses, which, as errors of electronic switches, can be eliminated only with great difficulty, lead to two types of image errors. In the one instance, interference signals result which lead to undesired transverse lines during image representation. In the other instance, the cross-talk pulses act as small transmitting pulses triggering echo signals particularly of the structures proximate the skin, which structures, immediately after the switchover, are represented in the form of ghost images in the visual image. Basically, the cited difficulties could be avoided by seeking a circuit plan wherein switching is carried out only subsequent to a preceding amplification; i.e., only in the case of high signal levels. However, this would lead to an undesired high component outlay, because, in the case of electronic focusing, a total of thirty independent channels would then have to be constructed.

It is more advantageous to maintain the present circuit plan and avoid interferences due to cross-talk pulses of the switches by virtue of the fact that the entire ultrasonic image is to be constructed of interleaved partial images such that blanking intervals alternately result in each partial image, in which blanking intervals it is possible to carry out switching operations without the influence of interference. The presently proposed circuit—or image construction— shall be explained in greater detail with reference to FIG. 4 on the basis of two partial images. FIG. 4 illustrates the partial image interleaving during simultaneous electronic focusing with a correspondingly conceivable association of transducer element columns with individual delay channels K. The interleaving of FIG. 4, however, can basically also be used in conjunction with pure natural focusing, the only difference being that transmitting—or receiving—surfaces having a smaller surface width as compared with electronic focusing are to be used.

Viewing FIG. 4, it is apparent that the image field comprising e.g. an image width of 12 cm and image depth of 18 cm, in the case of an array 1 which is approximately 16 cm long, is subdivided into a total of five image field regions or zones I through V. According to FIG. 4, the first partial image is to consist only of image field zones II, IV, and V. The size of the effective receiving surface for echo signals which is to be associated with the individual receiving surfaces is also indicated in the visual display image by the number of illustrated active transducer elements with the designation E for reception. The corresponding also applies to the transmit surface at the upper image edge characterized by S. Thus e.g. for the first partial image with a transmit surface of 3×10 transducers, the maximum receiving surface (in the case of additional electronic focusing) amounts to a total 3×20 individual transducers in zone V. In zone IV, the receiving surface has been reduced to a total of 3×14 individual transducers. The smallest receiving surface in the first partial image; namely that of zone II, exhibits only a total of four remaining active transducer elements of the center transducer element row of array 1. As implied by the showing of FIG. 4, the center line of 3×10 transmitting surface S coincides relative to array 1 with the center lines of the receiving surfaces shown directly therebelow. Thus, for a first scanning line of the first partial image, transducer element columns number six through number fifteen may be activated with the axis of symmetry between columns number ten and eleven. Similarly, during receiving mode II, transducer elements of the center row of columns nine through twelve would be activated; in receive mode IV, transducer element columns number four through seventeen would be activated; while in receive mode V, transducer element columns one through twenty would all be active. Similarly, during construction of the second partial image line by means of the transmit pulse from the 2×2 transmit surface shown to the right in FIG. 4, transducer elements of columns ten and eleven may be activated. Then, during receive mode I, these same transducer element columns are active, while during receive mode III, columns number seven through fourteen are active. Thus, as will hereafter be explained, the illustration in FIG. 4 of the center line of the 2×2 transmitting surface as widely spaced from the 3×10 transmitting surface is for clarity only, and a multiple line jump mode of partial image scanning is not being illustrated, since for example the center line of the first transmit surface of the first partial image and of the first transmit surface of the second partial image may actually coincide so that the successive lines of the first and second partial images may actually represent a single composite line within the scanning field, such composite line as displayed being composed of two raster lines on the display with a separation (if any) on the display which corresponds to not more than one-half the interval between composite scanning lines in the scanning field represented in FIG. 4.

In the first partial image, zones I and III represent blanking intervals which are utilized for the purpose of switching over the surface patterns (transmission, receiving zone II, receiving zone IV). No blanking interval is necessary at the transition between zones IV and V, because, given additional electronic focusing, it is possible here to switch into a total of eight channels immediately after amplification of the echo signals (by amplifiers 38). In FIG. 4, the second partial image consists only of two zones I and III which serve the purpose of writing (or recording) the image in the blanking intervals of the first image. Regarding the second partial image, zone II now represents a blanking interval. The second partial image has a substantially lesser penetration depth than the first partial image, so that the image construction time required here remains small. However, the maximum obtainable image frequency drops slightly from, for example, approximately 70 Hz to 50 Hz due to the increased time requirement for the second partial image. The chronological composition of the total image from the two partial images according to FIG. 4 may proceed in different ways depending upon the choice of line structure. A first variant makes possible a simple and hence a rapid programming of the three shift registers 9, 14 or 72. A reprogramming of the long register 9 or 72 is only necessary in the rhythm (or cadence) of the slower image frequency, whereas the shifter pulse rate corresponds to the high line frequency. Only shift register 14 is rapidly reprogrammed. The cited first variant results during image recording in the pure interlaced scanning process; i.e., for example, the first partial image is first completely recorded, and subsequently, the first recorded partial image is supplemented by the second partial image. However, in the case of this simple interlaced scanning process, the production of the second partial image, on account of the low image depth, raises the problem that echos e.g. emanating from a greater depth are, under certain circumstances, represented on adjacent lines on account of the sonic beam width which is greater in relation to the line spacing. If the given operating frequency is 2 MHz, these echos, in the case of normal body tissue, are namely only approximately 28 dB amplitude-weaker than echos of the structure proximate the skin which is to be represented. In order to ensure that images of deeply-disposed tissue are not represented in this manner as displaced in proximity to the surface, an amplitude interval of at least 50 dB should be provided. This condition can be adhered to e.g. by increasing the operating frequency, for example, from 2 MHz to 4 MHz. However, aid can also be found in the case of a maintained 2 MHz-operating frequency by using a line jump scanning process which, in a modification, makes possible leaps (or jumps) within the individual lines, said leaps having such spatial intervals that echos emanating from a great depth are from the very start incapable of being associated with the wrong line. However, the latter possible solution requires a considerable increase in technical outlay in view of a correspondingly enlarged complexity of the programming. However, within the framework of the present invention, a second variant which avoids the line jump process is given preference. This variant consists in that respectively associated lines of the first partial image and the second partial image are produced in direct chronological succession. The interleaving of the respective lines of both partial images can proceed such that both lines are represented directly one above the other or in direct proximity adjacent one another. This type of partial image interleaving provides virtually no transition difficulties, since echos emanating from the greatest image depth are already attenuated by approximately 74 dB given the operating frequency of 2 MHz, and, during the transition in each case from one line of the second partial image to the adjacent line of the first partial image, possible interfering echos are already more strongly attenuated by approximately 34 dB than the desired echos, taking into consideration blanking zone I. However, additional refinement can be achieved by virtue of the face that, in the case of the second partial image, operation is carried out with weaker transmit pulses, which is possible due to the lesser penetration depth of the second partial image. Thus, if the transmit pulse of the second partial image is, for example, selected to be approximately 20 dB lower than that of the first partial image, the echos are then likewise approximately 20 dB weaker. In toto, there thus results a satisfactory signal-to-noise ratio of approximately 54 dB in the case of the proposed operating frequency of 2 MHz. The conditions become yet more favorable if the operating frequency is correspondingly increased, because tissue attenuations are greater. The above stated signal-to-noise ratio of approximately 74 dB during transition from he first partial image to the second partial image merely represents a maximum value. Obviously, the drop in the power level in the case of the second partial image must be compensated by a corresponding greater amplification. However, as a consequence, the signal-to-noise ratio for the transition from the first partial image to the second partial image again drops from 74 dB to approximately 54 dB. Thus, comparable conditions regarding the signal-to-noise ratios result in the case of both image transitions.

Image construction with an additional concomitant electronic focus proceeds in partial steps on the basis of FIGS. 1 through 4 as follows: (1) Twenty bits are inserted into the first twenty register stages (e.g. at the extreme left) of shift register 9, whereby the position of image line number one is defined. In the case of shift register 14, ten bits are placed in the center of the register. Shift register 72 is programmed once in accordance with the requirements of the symmetry axis of the sonic field. (2) The transmit pulse follows. (3) At some time during the construction of the first line of the first partial image; for example, during the time corresponding to image zone I of the first scanning operation, shift register 14 receives two bits in register center. Via logic 15, the transmit switches 8 are adjusted such that all the bars of the bar-matrix 5 are open; i.e., not short-circuited. (4) Reception now takes place in zone II. The definition of the receiving width proceeds by means of selection of the channels (switching after amplification). (5) Regarding shift register 9, the connection of the two outer transducer rows in image zone III proceeds via logic 10 through 13. (6) Reception of zone IV takes place pursuant to a corresponding selection of the channels. (7) Reception of zone V. (8) A release of the register data of shift register 14 takes place via logic 15 for the purpose of adjusting the transmit switches 8, by means of the register data introduced per step (3), to the reduced transmitting surface of the first line of the following second partial image. (9) Subsequently transmission takes place with approximately 1/10 of the previous transmit pulse amplitude. (10) Reception now takes place in zone I, whereby the signal amplification has been increased by a factor of 10 as compared with previously. (11) With the receiving adjustment (or setting) in zone II, shift register 14 receives ten bits for the following line position. Logic 15 here prevents the forwarding (or transfer) of the new data to the transmit switches 8. (12) Reception of image zone III takes place pursuant to a corresponding selection of the channels. (13) The register contents of shift register 9 is advanced by one clock pulse (1 bit) in the entire block. The corresponding occurs with the register contents of shift register 72. Regarding shift register 14, adjustment (or setting) of the transmit switches 8 proceeds in accordance with the new register contents adjusted (or set) with step (11) above. (14) Continuation in this manner proceeds until the last image line has been scanned.

Figure 5:
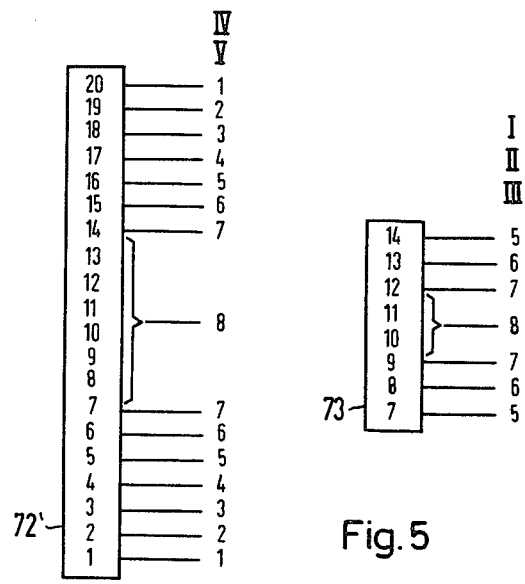
FIGS. 5 and 6 illustrate control programs for controlling particularly the electronic focusing so as to require the least amount of time-consumption and the least amount of circuit complexity.
Figure 6:
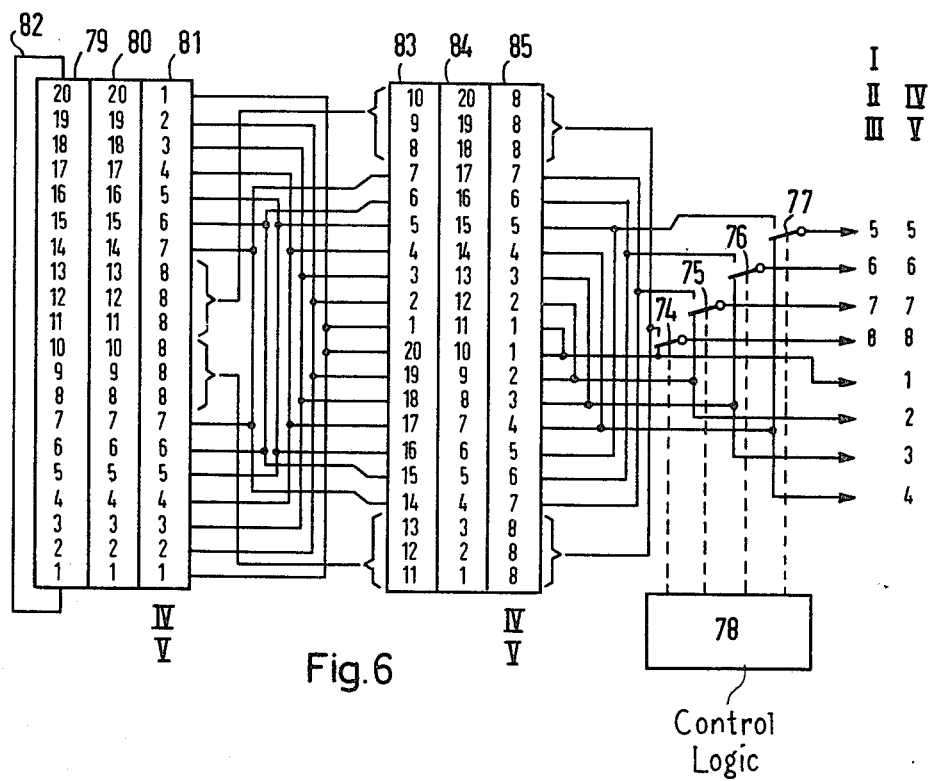

The intended simplification in the image construction results in an increased complexity of necessary program changes in the shift register. In particular, the long shift register 72 must also be reprogrammed with line frequency. However, this problem can be solved in a simple manner with distinct means. By way of example, one possible solution consists in that, in order to more rapidly reprogram shift register 72, the feeding of the shift register proceeds in a parallel operation via a plurality of feed lines. A second possiblility consists in a particular arrangement of the register locations in conjunction with a change in the allocation of the channels and the delay lines (or paths). An advancement of the recorded register contents by ten pulse steps is then sufficient for the purpose of reprogramming. The third possibility, wherein it is possible to dispense entirely with reprogramming, consists, as previously indicated, in an increase in the number of channels from a total of 8, to 10, taking into account a corresponding increase in the technical outlay. Of all the possibilities indicated, possibility two is of particular interest with regard to minimizing the cost of the switching structure and programming. If, for reasons of reducing technical outlay, only eight channels are selected instead of e.g. ten channels, the allocation of the array columns to the individual channels during construction of an image line must be changed. The most favorable selection possibility of a corresponding allocation of transducer element columns to channels is apparent from FIG. 5. Accordingly, only two allocations are necessary, the one of which having to be adjusted in the image zones IV and V, whereas the other must be adjusted in the zones I, II, III. The corresponding allocation is determined by the program contents of shift register 72. In FIG. 5, the digits inside the blocks 72' or 73, respectively, each designate numbers of transducer element columns. The digits to the right of the blocks represent the respective associated channel allocations in the zones IV or V, respectively, with regard to the transducer columns of block 72', and the respective associated channel allocations of zones I, II or III, with regard to the transducer columns of block 73. In the case of shift register 72, the simplest possibility of reprogramming would consist in occupying the entire shift register comrising 160 locations (or places) with new data in each particular instance. In the case of a clock pulse frequency of 2.5 MHz, which is a sensible maximum for MOS circuits, this would still take up $0.4 \times 160 = 64$ μsec (corresponding to barely 5 cm penetration depth), so that the image frequency would have to be correspondingly reduced. Only ten steps suffice (corresponding to 4 μsec) if shift register 72 is fed back (or coupled back) into itself at intervals of twenty register locations, respectively, and if four additional analog switches are provided. FIG. 6 illustrates the latter possibility in a field of a total of twenty array-columns. The additional analog switches are referenced with numerals 74 through 77; the respective control logic is referenced with 78. In the right hand block illustration of 79 through 81, the allocation of the array-columns to the channels is shown, as these allocations are required for image zones IV and V. The digits of the blocks 79 and 80, in turn, denote the numbers of register locations, and the numbers of allocated transducer columns. The digits of block 81, in contrast thereto, denote the numbers of corresponding allocated channels of the zones IV or V, respectively. Reference numeral 82 designates the previously cited feedback line of shift register 72. In the shift register, the [consecutive] sequence of the data bits is fundamentally maintained, so that a fixed allocation between the shift register places and the channels remains. However, if, after twenty bits in each particular instance, the shift register is finally fed back (or back-coupled) and the register contents are correspondingly advanced ten clock pulses, the [respective] allocation of array-columns and channels results as illustrated in blocks 83 through 85 to the right. The similarity with the desired (or target) configurations (for image zones I, II, III) is immediately apparent. However, a transposition (or interchange) of channels as compared with the desired allocation is still present. Given a suitable programming of the delay times, this problem could be regarded as solved. However, this requires a relatively large adjustment range of the delay lines. The additional channel changeover switches 74 through 77 of channels 5, 6, 7, or 8, respectively, make possible the correct allocation in the zones I, II, and III, with a relatively narrow adjustment range of the delay line. The correct channel allocations in the different zones I through V are specifically indicated at the output of the programming circuit diagram according to FIG. 6 through specification of the corresponding channel digits or numbers. In order to simplify the illustration, a more detailed explanation of the parallel displacement of the line (or horizontal) scanning has been omitted. On the whole, the latter operation is additively superimposed on the present actuating (or control) operations. In order to avoid switch-interference problems, it would also be advantageous to arrange the analog switches 74 through 77 behind non-illustrated channel amplifiers. This makes switching at a high level possible. Only then do the switchable (programmable) delay times ensue. With the simplified reprogramming of shift register 72 corresponding to the plan of FIG. 6, a modification in the time plan of the image construction results only in the following intermediate steps. Between the above-cited switching steps (5) and (6) there is inserted a switching step (5'), during which shift register 72, in the fed-back (or back-coupled) state, is advanced ten bits at a time. In addition, the channel-changeover switches 74 through 77 are also switched over in this switching step. An additional intermediate switching step results at the end of the preceding switching step (7). In this additional switching step (7'), shift register 72 is again advanced an additional ten bits. The construction of the second partial image is thus delayed by four microseconds (4 μsec). In addition, a repeated switch-over of channel-changeover switches 74 through 77 takes place. Regarding present step (12)—i.e., reception in image zone III, however, no additional intermediate step (or a corresponding image delay) is necessary, because the channel allocation adjusted (or set) by means of shift register 72 is also required for zone II of the next partial image.

SUMMARY OF OPERATION

Summarizing the operation of the embodiment of FIG. 4, during each transmit operation, a surface S is activated to emit an ultrasonic energy pulse. In the single echo-reception interval following a first transmit operation, the control means establishes a reception surface E at a predetermined switching time corresponding to phase II in FIG. 4, such receiving surface being of relatively small size adapted to receive echo signals returning in a common direction (normal to the array 1) from relatively close to said array (as measured along the transmit axis normal to the array). At a further predetermined switching time represented by phase IV in FIG. 4 the control means switches the array to present a receiving surface E of intermediate size adapted to receive echo signals returning in the common direction from an intermediate depth (as measured along the transmit axis). At a later predetermined switching time as represented by phase V in FIG. 4, during the same single echo-reception interval, the control means switches the array to provide a receiving surface of substantially greater size adapted to receive echo signals produced by the same ultrasonic energy pulse and returning in the common direction but from a substantially greater distance from said array (as measured along the transmit axis). Thus in receiving echo signals produced by a single ultrasonic energy pulse, the receiving surface E during a single echoes reception interval is sequentially increased in size as echoes arrive from progressively more remote distances from the array. Similarly during a second transmit interval, the control means switches the receiving surface E at predetermined switching times as represented by phase I and phase III in FIG. 4 so that the receiving surface is sequentially increased in size as echoes arrive from progressively more remote distances from the array during a single echo-reception interval.

It will be apparent that many modifications and variations may be effected without departing from the scope of the novel concepts and teachings of the present invention.

I claim as my invention:

1. Apparatus for ultrasonic scanning, comprising an ultrasonic applicator having variable depth of focus during a scanning operation, characterized in that the applicator comprises a plurality of transducer elements arranged spatially adjacent one another for activation in different combinations so as to define respective receiving surfaces of different sizes for effective reception of ultrasonic echo signals from different distance, and control means for automatically controlling the activation of the respective different combinations of said transducer elements of different size during a scanning operation, and operable for changing the number of active transducer elements from a low value to a maximum value, said control means comprising selector means operable for controlling selection of the number of transducer elements of a row which can be active as a block, and transmit control means for activating less than all of a block of transducer elements during transmit mode while accommodating activation of all of the block of transducer elements during received mode, said selector means comprising a first shift register (9) which is loaded with a number of bits to form a block of bits in accordance with the maximum number of transducer elements to be active as a block during a scanning cycle, the control means providing for a plurality of changes in the size of the receiving surface prior to each shifting of the block of bits in said shift register, successive blocks of surface pattern switches controlling coupling with successive sections of individual transducer elements, a series of matrix conductors (5) each connected with respective corresponding surface pattern switches of successive blocks thereof, transmit/receive energy switches (8) selectively controlling the supply of transmit energy to the respective matrix conductors, and said control means comprising a second shift register (14) controlling said transmit/receive switches (8) for determining the width of the transmitting surface defined by active transducer elements during emission of a transmit signal.

2. Apparatus according to claim 1, with a predetermined number of channels (41–47, 47') having amplifier means (48–55) and delay means (56–63) for providing a number of different electronic delay times, and switching means (64–71) interposed between the matrix conductors and said channels for connecting selected numbers of said matrix conductors to each of said channels.

3. Apparatus for ultrasonic scanning, comprising an ultrasonic applicator having a plurality of ultrasonic transducer elements arranged spatially adjacent one another for activation in different combinations to provide ultrasonic transducer surfaces of different sizes adjusted to scanning at respective depth-positions, and control means for automatically controlling the activation of the respective different combinations of said ultrasonic transducer elements to provide said ultrasonic transducer surfaces of said different sizes during a scanning operation, and operable for changing the number of active transducer elements from a low value to a maximum value, said ultrasonic transducer elements being arranged in rows one above another and in columns adjacent one another, said control means comprising line scanning block selection shift register means (9) enabling activation of a maximum number of columns of ultrasonic transducer elements as a block, and operable for shifting so as to enable activation of different sets of said columns representing different blocks of said ultrasonic transducer elements in successive transducer operating cycles with the successive blocks being displaced in the direction along said rows to effect a line scanning operation, said control means further comprising surface pattern switch means (4) operable in conjunction with said block selection shift register means to selectively activate a number of columns equal to said maximum number forming a block and to activate a number of rows equal to all of the rows of said ultrasonic transducer elements, thereby to provide a full multirow ultrasonic transducer surface, and said control means further comprising block limitation switch means (10–13, 8, 14) controlling activation of said transducer elements via said surface pattern switch means and operable for controlling such activation of said transducer elements via said surface pattern switch means to restrict the number of columns of said ultrasonic transducer elements to a number less than said maximum number and to restrict the number of rows to less than all of said rows, to thereby activate an ultrasonic transducer surface of a lesser size than said full multirow ultrasonic transducer surface while said block selection shift register means enables activation of a respective block of said ultrasonic transducer elements.

4. Apparatus according to claim 3, with said line scanning block selection shift register means comprising a first shift register (9) which is subjected to successive shift operations to enable successive blocks of said ultrasonic transducer elements with the successive blocks being offset in the direction along said rows by a number of columns which is less than said maximum number of columns which are enabled as a block, a series of matrix conductors (5) for coupling with said ultrasonic transducer elements under the control of said surface pattern switch means, said block limitation switch means comprising logic means (10-13) for controlling said surface pattern switch means to selectively block coupling of said matrix conductors with respective rows of said ultrasonic transducer elements thereby in conjunction with said first shift register to select a height for an active ultrasonic transducer surface which is less than the height of a multirow ultrasonic transducer surface corresponding to a fully multirow block as enabled by said first shift register (9), said block limitation switch means further comprising transmit energy switch means (8) for supplying transmit energy to said matrix conductors (5) and second shift register means (14) controlling said transmit energy switch means to control the number of said matrix conductors (5) which receive transmit energy, said second shift register means (14) being selectively operable to control said transmit energy switch means to supply transmit energy to a number of said matrix conductors equal to said maximum number forming a block, said being selectively operable to control said transmit energy switch means to supply transmit energy to a restricted number of matrix conductors less than said maximum number of activate an ultrasonic transducer surface of a width which is less than the width corresponding to a block of said ultrasonic transducer elements.

5. Apparatus according to claim 4, with a predetermined number of channels (41-47, 47') having amplifier means (48-55) and delay means (56-63) for providing a number of different electronic delay times, and switching means (64-71) interposed between the matrix conductors and said channels for connecting selected ones of said matrix conductors to each of said channels.

6. Apparatus according to claim 3, characterized in that the control means (4-17, or 38-72) is operable for activating combinations of said transducer elements for the purpose of constructing ultrasonic partial images (for example, according to FIG. 4) which are interleaved with one another.

7. Apparatus according to claim 6, characterized in that the control means activates successive combinations of said transducer elements for constructing a line of one ultrasonic partial image and then a line of another ultrasonic partial image in a chronologically interleaved fashion.

8. Apparatus according to claim 7, characterized in that the control means activates combination of transducer elements during the construction of successive lines of the respective ultrasonic partial images which combinations of transducer elements have closely adjacent axes of symmetry so that the partial image lines can be successively represented in proximity to one another in a visual display.

9. Apparatus according to claim 6, characterized in that the control means activates different combinations of transducer elements in constructing different partial images, and having different transmitting energies.

10. Apparatus according to claim 3, characterized in that the ultrasonic applicator comprises an area array of ultrasonic transducer elements having an arrangement in a transverse direction to define a scanning plane and the array exhibiting mechanical curvature with respect to a direction perpendicular to the scanning plane so as to provide for mechanical focusing with respect to the layer thickness direction.

11. Apparatus according to claim 3, with said ultrasonic applicator comprising an area array of ultrasonic transducer elements arranged in a plane surface, the control means providing for electronic focusing of said array.

12. Apparatus for ultrasonic scanning, comprising an ultrasonic applicator having a plurality of ultrasonic transducer elements arranged spatially adjacent one another for activation in different combinations to provide ultrasonic transducer surfaces of different sizes adjusted to scanning at respective depth-positions, and control means for automatically controlling the activation of the respective different combinations of said ultrasonic transducer elements to provide said ultrasonic transducer surfaces of said different sizes during a scanning operation, and operable for changing the number of active transducer elements from a low value to a maximum value, said ultrasonic transducer elements being arranged in rows one above another and in columns adjacent one another, said control means comprising line scanning block selection shift register means (9) enabling activation of a maximum number of columns of ultrasonic transducer elements as a block, and operable for shifting so as to enable activation of different sets of said columns representing different blocks of said ultrasonic transducer elements in successive transducer operating cycles with the successive blocks being displaced in the direction along said rows to effect a scanning operation, said control means further comprising surface pattern switch means (4) operable in conjunction with said block selection shift register means to selectively activate a number of columns equal to said maximum number forming a block and to activate a number of rows equal to all of the rows of said ultrasonic transducer elements, thereby to provide a full multirow ultrasonic transducer surface, and said control means further comprising block limitation switch means (10-13, 8, 14) controlling activation of said transducer elements via said surface pattern switch means and operable for controlling such activation of said transducer elements via said surface pattern switch means to reduce the number of activated ultrasonic transducer elements to a number less than said maximum number, to thereby activate an ultrasonic transducer surface of a lesser size than said full multirow ultrasonic transducer surface while said block selection shift register means enables activation of a respective block of said ultrasonic transducer elements.

13. Apparatus according to claim 12, with said line scanning block selection shift register means comprising a first shift register (9) which is subjected to successive shift operations to enable successive blocks of said ultrasonic transducer elements with the successive blocks being offset in the direction along said rows by a number of columns which is less than said maximum number of columns which are enabled as a block, a series of matrix conductors (5) for coupling with said ultrasonic transducer elements under the control of said surface pattern switch means, said block limitation switch means comprising logic means (10–13) for controlling said surface pattern switch means to selectively block coupling of said matrix conductors with respective rows of said ultrasonic transducer elements thereby in conjunction with said first shift register to select a height for an active ultrasonic transducer surface which is less than the height of a multirow ultrasonic transducer surface corresponding to a full multirow block as enabled by said first shift register (9), said block limitation switch means further comprising transmit energy switch means (8) for supplying transmit energy to said matrix conductors (5) and second shift register means (14) controlling said transmit energy switch means to control the number of said matrix conductors (5) which receive transmit energy, said second shift register means (14) being selectively operable to control said transmit energy switch means to supply transmit energy to a number of said matrix conductors equal to said maximum number forming a block, and being selectively operable to control said transmit energy switch means to supply transmit energy to a restricted number of matrix conductors less than said maximum number to activate an ultrasonic transducer surface of a width which is less than the width corresponding to a block of said ultrasonic transducer elements.

14. Apparatus according to claim 13, with a predetermined number of channels (41–47, 47') having amplifier means (48–55) and delays means (56–63) for providing a number of different electronic delay times, and switching means (64–71) interposed between the matrix conductors and said channels for connecting selected ones of said matrix conductors to each of said channels.

15. Apparatus according to claim 12, characterized in that the control means (4–17, or 38–72) is operable for activating combinations of said transducer elements for the purpose of constructing ultrasonic partial images (for example, according to FIG. 4) which are interleaved with one another.

16. Apparatus according to claim 15, characterized in that the control means activated successive combinations of said transducer elements for constructing a line of one ultrasonic partial image and then a line of another ultrasonic partial image in a chronologically interleaved fashion.

17. Apparatus according to claim 16, characterized in that the control means activates combination of transducer elements during the construction of successive lines of the respective ultrasonic partial images which combinations of transducer elements have closely adjacent axes of symmetry so that the partial image lines can be successively represented in proximity to one another in a visual display.

18. Apparatus according to claim 15, characterized in that the control means activates different combinations of transducer elements in constructing different partial images, and having different transmitting energies.

19. Apparatus according to claim 12, characterized in that the ultrasonic applicator comprises an area array of ultrasonic transducer elements having an arrangement in a transverse direction to define a scanning plane and the array exhibiting mechanical curvature with respect to a direction perpendicular to the scanning plane so as to provide for mechanical focusing with respect to the layer thickness direction.

20. Apparatus according to claim 12, with said ultrasonic applicator comprising an area array of ultrasonic transducer elements arranged in a plane surface, the control means providing for electronic focusing of said array.

* * * * *